US007687027B2

(12) United States Patent
McGill

(10) Patent No.: US 7,687,027 B2
(45) Date of Patent: Mar. 30, 2010

(54) CLEANING COMPOSITIONS, METHODS AND MATERIALS FOR REDUCING NUCLEIC ACID CONTAMINATION

(75) Inventor: Eric McGill, Joppa, MD (US)

(73) Assignee: Becton, Dickinson and Company, Franklin Lakes, NJ (US)

(*) Notice: Subject to any disclaimer, the term of this patent is extended or adjusted under 35 U.S.C. 154(b) by 0 days.

(21) Appl. No.: 12/038,738

(22) Filed: Feb. 27, 2008

(65) Prior Publication Data

US 2009/0215660 A1 Aug. 27, 2009

(51) Int. Cl.
*A61L 2/18* (2006.01)
*C12Q 1/68* (2006.01)
*B08B 3/04* (2006.01)
*C11D 3/37* (2006.01)

(52) U.S. Cl. ......................... 422/28; 510/161; 510/384; 510/391; 510/433; 510/470; 510/504; 134/22.19; 134/39; 134/42; 435/6

(58) Field of Classification Search ................ 510/161, 510/384, 391, 433, 470, 504; 134/22.19, 134/39, 42; 422/28; 435/6
See application file for complete search history.

(56) References Cited

U.S. PATENT DOCUMENTS 4,751,078 A * 6/1988 Nagabhushan et al. ...... 530/351
5,858,650 A 1/1999 Celebuski
6,248,522 B1 6/2001 Haberhausen et al.
6,391,835 B1 5/2002 Gott et al.
6,841,393 B2 * 1/2005 Koenig ....................... 436/526
7,048,806 B2 5/2006 Ochomogo et al.
2002/0165124 A1 11/2002 Nguyen
2003/0092171 A1 5/2003 Henck
2003/0165943 A1 * 9/2003 Oelmuller et al. .............. 435/6
2004/0101881 A1 5/2004 Durmowicz et al.
2005/0202491 A1 9/2005 Nelson et al.
2007/0281356 A1 12/2007 Shinkai et al.

FOREIGN PATENT DOCUMENTS

CA 2604223 * 11/2006
WO WO-95-14790 A1 6/1995
WO WO-2005-087951 A2 9/2005
WO WO-2007-044520 A1 4/2007

OTHER PUBLICATIONS

Dorris Ph.D.,Mark, Reversing the Effects of Formalin Fixation, Thesis 1999, Chapter 3, Chapter 4, Appendix 1, pp. 1-9, 1999.

(Continued)

*Primary Examiner*—Brian P Mruk
(74) *Attorney, Agent, or Firm*—Lerner, David, Littenberg, Krumholz & Mentlik, LLP

(57) ABSTRACT

The present invention relates to methods using cleaning compositions for the reduction of nucleic acid contamination. More particularly, the present invention relates to cationic compositions that bind to, and can remove, extraneous nucleic acids, polynucleotides, and DNA from the surface of a substrate. Preferably, the cationic compositions include a substance with a molecular weight of 500 Da or more. The present invention finds utility as a surface decontamination agent in PCR and other related DNA amplification techniques.

7 Claims, 2 Drawing Sheets

OTHER PUBLICATIONS

Murphy, J.C., et al., "RNA Isolation and Fractionation with Compaction Agents," Analy. Biochem., vol. 295, pp. 143-148 (2001).

Wang, G., et al., "Bacterial DNA decontamination for reverse transcription polymerase reaction (RT-PCR)," J. Microbiol. Methods, vol. 51, pp. 119-121 (Mar. 2002).

Mohammadi, T., et al., "Removal of contaminating DNA from commerical nucleic acid extraction kit reagents," J. Microbiol. Methods, vol. 61, pp. 285-288 (2005).

* cited by examiner

CLEANING COMPOSITIONS, METHODS AND MATERIALS FOR REDUCING NUCLEIC ACID CONTAMINATION

BACKGROUND

The decontamination of nucleic acids from surfaces that are used in the Polymerase Chain Reaction (PCR) technique, and other related nucleic acid amplification techniques, is extremely important. This is because PCR (and related techniques) may amplify extraneous nucleic acids that, for example, remain from a previous amplification. This can lead to false positive results, for example mistyping of a genotype.

In prior art methods of surface decontamination, expensive, difficult to handle solutions have generally been employed as the decontamination agent. In most cases, additional steps which involve cleaning the decontamination reagent residue are also required. In addition, amplicon decontamination solutions and methods previously used in sensitive environments are inconsistent and unreliable. It is not uncommon to test and find persistent contamination after decontaminating using prior art methods and compositions.

This is due to a number of factors. The prior art suggests that many of the commonly available compositions, such as Eliminase, DNA Away™, and bleach, do not consistently and effectively degrade amplifiable nucleic acids. The prior art also suggests that most of the commonly used methods, which involve using one or more cleaning compositions to wet and then wipe contaminated surfaces actually only partially remove the contaminating nucleic acids while spreading or missing the remainder. Thus, there is a need in the industry for an improved decontamination process that is inexpensive, easy to use, and that utilizes user-friendly reagents.

DETAILED DESCRIPTION OF THE INVENTION

Figure 1:
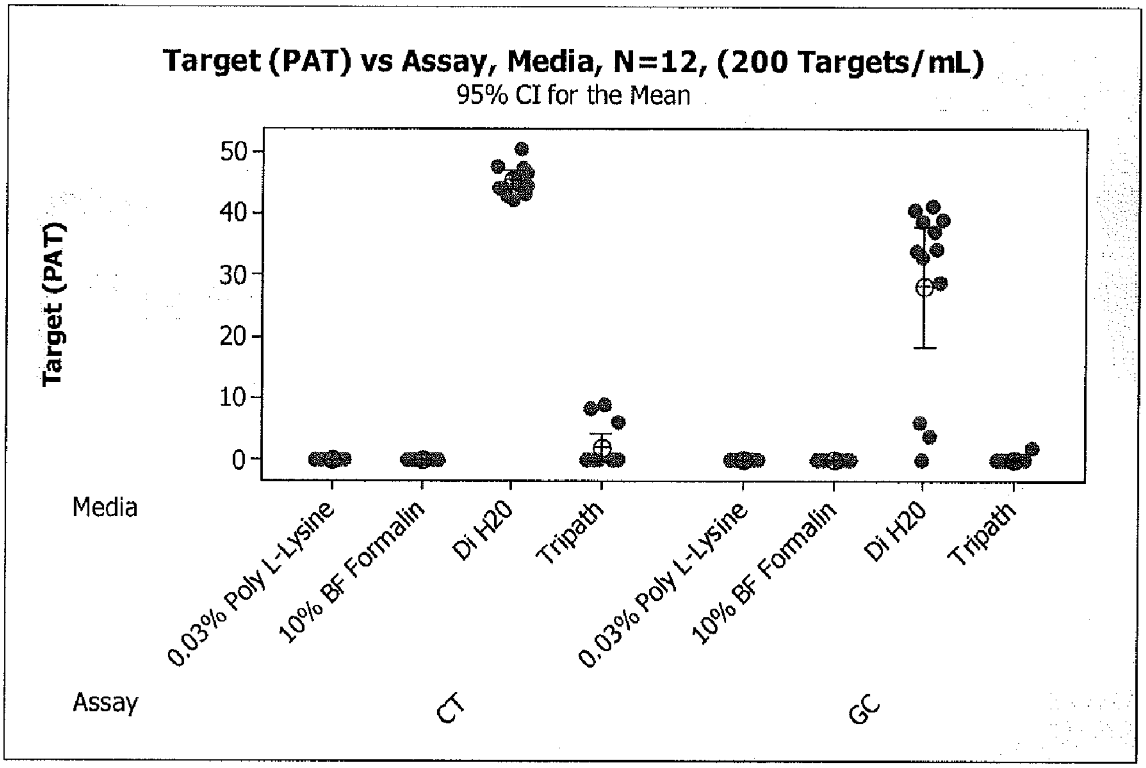
FIG. 1 shows Target (PAT) vs. Assay for various media.

The present invention relates to a method of reducing nucleic acid contamination on a surface by contacting the surface to be decontaminated with a substance containing a cationic compound. Without being bound by any theory of the invention, it is believed that the cationic substance interacts with negative charges in the nucleic acid to non-specifically (i.e., not in any sequence dependent maiuer) bind the nucleic acid.

Reducing nucleic acid contamination or nucleic acid "decontamination" as used herein refers to altering nucleic acids in a way that makes them, for example, no longer capable, or less capable, of acting as a template in an amplification reaction. Decontamination generally renders the nucleic acids incapable, or less capable, of interfering with other amplification reactions.

Reducing contamination or decontamination also refers to reducing the ability of, or preventing, the nucleic acid from binding to another nucleic acid, protein, or other biological substance. Reducing nucleic acid contamination or nucleic acid decontamination also refers to preventing, or making the nucleic acids less capable of, serving as a substrate for an enzyme. Reducing nucleic acid contamination or nucleic acid decontamination as used herein does not refer to any particular mechanism by which the reduction in contamination, or decontamination, occurs. The cationic substance may be a solution or a coating on the surface of a filter or fabric material. The cationic substance may be any organic substance, and can be either low or high molecular weight. Preferably, the invention relates to the use of cationic compositions with a molecular weight of at least 500 Da. In an even more highly preferred embodiment, this invention is directed to the use of compositions which include at least one cationic polymer with a molecular weight between 500 Da and 50 kDa. This invention encompasses using combinations of low molecular weight and high molecular weight cationic substances.

Preferred methods involve wiping the surface with a cloth or wipe that contains cationic substances which have a high binding affinity for negatively charged nucleic acids and will improve the uptake and retention efficiency during the cleaning process. The cationic materials will attract the nucleic acids when proximal to them and lessen spreading due to the higher binding affinity. Additionally, using a cleaning solution, preferably one that also contains a cationic substance(s) to solubilize a contaminating nucleic acid and loosen it from a surface before binding the contaminating nucleic acid to a trapping surface such as a sponge or wiping cloth will increase the efficiency even more.

This invention involves using materials and compositions containing cationic substances to improve the process of decontaminating surfaces that are contaminated with nucleic acids (amplicons). Materials and compositions containing cationic substances have a greater binding affinity for nucleic acids on surfaces than those without these substances because of the negative charge possessed by the nucleic acids. Hence, materials and compositions containing cationic substances will more readily attract, bind and retain nucleic acids than materials and compositions that do not contain cationic substances.

The present invention thus relates to a method of reducing nucleic acid contamination on a surface by way of contacting the surface to be decontaminated with a substance containing at least one cationic compound.

More preferably, the invention relates to the use of cationic compositions with a molecular weight of at least 500 Da. In an even more highly preferred embodiment, this invention is directed to the use of compositions which include a cationic polymer with a molecular weight between 500 Da and 50 kDa.

The nucleic acids that may be cleaned with the present compositions, materials, and methods would include any that would typically contaminate a surface in a laboratory setting. This would include, but is not limited to, DNA, RNA, modified nucleic acids, and peptide nucleic acids. The nucleic acids may, for example, be mRNAs, oligonucleotides, primers, probes, plasmid DNA, bits of generic DNA and the like. The nucleic acids may be in an impure form, e.g. arising from a spilled biological sample.

The surfaces that can be treated would include any that would typically be present in a laboratory setting. This would include plastic surfaces, steel surfaces, ceramic surfaces, and surfaces that have a variety of textures including sealed or porous. This would also include surfaces on instruments, such as for example, thermocyclers.

The invention may also find use during sample collection, e.g., in a forensic setting surfaces surrounding the sample may be cleaned, and the surface of the sample might be cleaned, as well, if a further sample is to be taken from an interior portion.

Cationic substances. Cationic substances suitable for use in this invention include generally any organic or inorganic cationic substance. The cationic substance may have one or more charge sites in the molecule. Preferably, the cationic substance has only positive (+) charge sites, however zwitterionic substances may also be used. The cationic substances may be of low or high molecular weight. The invention is especially directed to the use of cationic medium to high molecular weight organic polymers. The invention also encompasses combinations of cationic medium to high molecular weight polymers and organic or inorganic small molecules.

Many cationic organic or inorganic small molecules are known in the art that can be utilized with this invention. The small molecule cationic substances can include among other things organic and inorganic salts, soaps, surfactants, detergents, small inorganic molecules, and transition metal complexes. However, generally, any cationic small molecule known in the art can be used.

Preferably the cationic medium to high molecular weight substances have a molecular weight of at least 500 Da. More preferably, this invention is directed to the use of cationic compositions which include a cationic polymer with a molecular weight greater than about 500 Da. The cationic polymer will generally have a molecular weight between 500 Da and 50 kDa. In certain aspects, cationic polymers perform unexpectedly better than small molecule substances. Cationic polymers suitable for use with this invention include Poly-L-Lysine and/or other poly-cationic amino acids, Chitosan and/or other poly-cationic polysaccharides, POLECTRON® 430 (by International Specialty Products), and polyethylene imines (such as Lupasol by BASF). Typically, the cationic polymer is present in solution at a concentration of about 1%-10%. More preferably, the concentration is about 3%-5%. The solvent can be any that is capable of dissolving both the polymer and the DNA. Preferably the solvent will dissolve nucleic acids as well as the polymer. Preferably the solvent is nontoxic, and with a boiling point that allows for evaporation at room temperature.

Cationic amino acids suitable for use with this invention include polyamino acids that are predominantly in the cationic form. This can include an amino acid that is in a dipolar form. Preferably, the cationic poly amino acids used in the present invention are in solution with a pH that is below the isoelectric point of the amino acid.

Cationic polysaccharides for use in the invention include naturally occurring cationic polysaccharides, as well as polysaccharides and polysaccharide derivatives that have been made cationic by chemical means. This can include, for example, quarternization with various quaternary amine compounds containing reactive chloride or epoxide sites. Examples of cationic polysaccharides include, but are not restricted to, cationic guar, cationic hydroxyethyl cellulose and cationic hydrophobically modified hydroxyethyl cellulose. See e.g., U.S. Pat. Nos. 4,663,159; 5,037,930; 5,473,059; 5,387,675; 3,472,840 and 4,031,307, each of which are herein incorporated by reference in their entireties.

Lupasol SC-61B & Lupasol SC-62J are hydroxyethylated, (ethoxylated) water soluble polyethylene imines formed by a reaction of relatively high molecular weight polyethylene imines with ethylene oxide. In Lupasol SC-61B & Lupasol SC-62J, approximately eighty percent of the available amine hydrogens of the base polymer have been converted to hydroxyethyl groups.

Chitosan is a linear polysaccharide composed of randomly distributed β-(1-4) -linked D-glucosamine (deacetylated unit) and N-acetyl-D-glucosamine (acetylated unit). Chitosan is produced commercially by deacetylation of chitin (can be produced from chitin also), which is the structural element in the exoskeleton of crustaceans (crabs, shrimp, etc.). The degree of deacetylation (% DA) can be determined by NMR spectroscopy, and the % DA in commercial chitosans is in the range 60-100%. The amino group in chitosan has a pKa value of about 6.5. Thus, chitosan is positively charged and soluble in acidic to neutral solution with a charge density dependent on pH and the % DA-value. Preferably, the chitosan is in acidic solution. Chitosan is bioadhesive and readily binds to negatively charged entities.

Cloths, wipes, sponges and filters. In one embodiment the cationic substances of this invention are incorporated into a cloth, sponge, pad or wipe that has been impregnated with or coated with the cationic substance or composition. These generally include any absorbent cloth or wipe that is used in the laboratory. This also includes, but is not limited to, cotton swabs, woven fiber pads, or wipes made of filter paper. Specific examples would include Kimwipes®, and WypAll® Utility-Wipes, manufactured by Kimberly-Clark Corporation. In addition, ordinary sponges or absorbent cloth can be impregnated with a cationic substance, and such embodiments are contemplated by this invention as well.

Nucleic acid contaminants also exist as aerosols or upon dust particles. Thus, air filters that have a cationic substance incorporated onto them are also contemplated. Such filters can be prepared, for example, by dipping the filter material into a solution containing the cationic substance and then drying the filter.

Layered filters and membrane filters can also be used in accordance with the present invention. A multi-layered filter can be formed, for example, by placing polymeric sheets in between particulate filters. In addition a filter may be made by first producing filter material with the cationic substances incorporated onto it, and then forming the material into a filter.

Kits. Kits are provided for nucleic acid decontamination in an embodiment of this invention. The kits comprise a cationic substance (as herein described) optionally contained in a delivery device, and a cloth, wipe, sponge or filter. In another embodiment the kits only include the cloth, wipe, sponge, or filter impregnated or coated with a cationic substance. The decontamination agent is provided in the form of a solution in one embodiment, wherein the solution contains the cationic substance.

The kits optionally contain one or more receptacles for the decontamination solution, and the cloth, wipe, sponge and/or filter. The kits can also optionally include instructions, and other reagents for performing a nucleic acid amplification reaction.

In a preferred embodiment the kit comprises: a cationic polymer in solution with a molecular weight between about 500 Da and 50 kDa, wherein the solution is contained in a delivery device which can spray the solution onto a surface; and a cloth, wipe, sponge, or filter.

EXAMPLE

The BD® Vipers uses an extraction system based on iron oxide. Iron oxide contains a net positive charge in acidic solutions and a net negative charge in basic solutions. This versatility allows for both binding and eluting of negatively charged nucleic acid.

Poly-L lysine is a polymeric macromolecule that is used to facilitate adherence of patient tissue sample to glass surfaces. It is poly-cationic and will readily bind negatively charged particles such DNA. Formaldehyde can also act as a carbocation and bind negatively charged particles such as nucleic acids. Without wishing to be bound by any specific theory, it is presently theorized that these compounds are competing with the iron oxide and binding target molecules. Subsequently, a significant amount of target is bound to these substances and lost, as these substances are removed during the extraction process.

In this experiment, poly-L lysine, formaldehyde and a sample transport medium believed to contain one or both of those compounds, Tripath, is evaluated to observe for inhibition of the extraction system. The organisms used in this experiment are *Chlamydia trachomatis* (CT) and *Neisseria gonorrheae* (GC).

FIG. 1 shows complete inhibition of the system in the presence of 0.03% poly-l-lysine, 10% buffered formalin and the Tripath media. The control, sample in just de-ionized water, is not inhibited.

The IAC or internal amplification control is an amplifiable nucleic acid sequence present in the assay microwells, but not during the extraction process. Its purpose is to demonstrate that conditions for amplification are either suitable or inhibited. If the IAC is amplified, then the sample nucleic acid target should be amplified, unless inhibition occurred during the extraction process. If the IAC is not amplified, then the sample nucleic acid should also be inhibited in assay.

Figure 2:
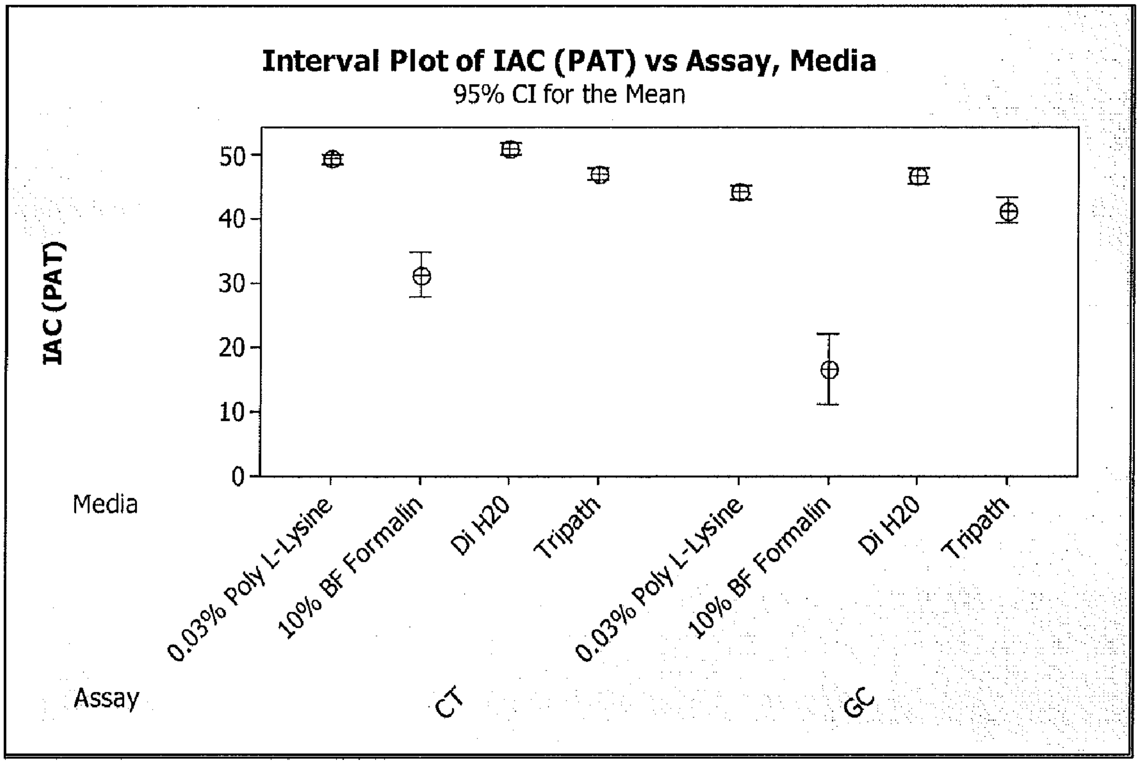
FIG. 2 shows an interval plot of internal amplification control (IAC) vs. Assay in various media.

In this experiment the IAC is significantly inhibited but not completely inhibited in the presence of 10% buffered formalin like the inhibited extracted sample. See FIG. 2. This suggests that a small amount of the formalin made its way into the assay from the extraction, but not enough to completely shut down the assay. The IAC is slightly inhibited in the presence of the poly-l-lysine and Tripath media, which suggests that most of the poly-l-lysine was removed before transfer of the eluted sample to the assay, and that inhibition of the extracted sample occurred during extraction.

Extraction of CT and GC nucleic acid target are completely inhibited in the presence of 0.03% Poly L-Lysine and 10% Neutral Buffered Formalin. Extraction is severely inhibited in the Tripath media for GC target and significantly inhibited for CT target.

Amplification is significantly negatively impacted by carryover of the neutral buffered formalin into the both assays and slightly negatively impacted in the poly 1-lysine and Tripath media. The presence of ferrous sulfate improves performance in the Tripath media. Inhibition is likely due to binding of the target nucleic acids by the positively charged poly-l-lysine and formaldehyde.

I claim:

1. A method of reducing nucleic acid contamination on a surface comprising: contacting the surface to be decontaminated with a solution comprising a dissolved ethoxylated water soluble polyethylene imine with a molecular weight of at least 500 Da.

2. The method of claim 1, wherein the molecular weight of the ethoxylated water soluble polyethylene imine is between 500 Da and 500 kDa.

3. The method of claim 1, wherein the molecular weight of the ethoxylated water soluble polyethylene imine is between 70 kDa and 300 kDa.

4. A method of reducing nucleic acid contamination on a surface comprising: contacting the surface to be decontaminated with a solution comprising Poly-L-lysine with a molecular weight of at least 500 Da.

5. The method of claim 4, wherein the solution concentration of ethoxylated water soluble polyethylene imine is between 1% and 10%.

6. The method of claim 4 wherein the solution concentration of ethoxylated water soluble polyethylene imine is between 3% and 5%.

7. The method of claim 1, wherein the solution is present on a laboratory swab, wipe, cloth, filter, or sponge.

* * * * *